United States Patent [19]

Koike et al.

[11] Patent Number: 5,453,549

[45] Date of Patent: Sep. 26, 1995

[54] HEXAFLUOROPROPYLENE OXIDE OLIGOTHER DERIVATIVE AND PROCESS FOR MANUFACTURE THEREOF

[75] Inventors: Noriyuki Koike, Yoshii; Kouichi Yamaguchi, Takasaki; Hiromasa Yamaguchi; Kouji Takano, both of Annaka, all of Japan

[73] Assignee: Shin-Etsu Chemical Co., Ltd., Tokyo, Japan

[21] Appl. No.: 57,775

[22] Filed: May 6, 1993

[30] Foreign Application Priority Data

May 29, 1992 [JP] Japan .................................. 4-164134

[51] Int. Cl.$^6$ ............................................ C07C 43/18
[52] U.S. Cl. ................................... 568/615; 568/685
[58] Field of Search .................................. 568/615, 685

[56] References Cited

U.S. PATENT DOCUMENTS 4,987,267  1/1991  Takaoka et al. .

FOREIGN PATENT DOCUMENTS 538061   4/1993  European Pat. Off. ............... 568/615
1578003  8/1969  France .

OTHER PUBLICATIONS

European Search Report dated Aug. 25, 1993.

*Primary Examiner*—Johann Richter
*Assistant Examiner*—Kimberly J. Kestler
*Attorney, Agent, or Firm*—Finnegan, Henderson, Farabow, Garrett & Dunner

[57] ABSTRACT

An extremely reactive and highly copolymerizable hexafluoropropylene oxide oligoether derivative, to give bi- or ter-polymers with fluoroolefins and perfluoroalkyl vinyl ethers, which is represented by general formula:

$$F\!-\!(CFCF_2O)_{n-1}\!-\!CFCF_2\!-\!CH\!=\!CH_2$$
$$\phantom{F\!-\!(}|\phantom{CFCF_2O)_{n-1}\!-\!}|$$
$$\phantom{F\!-\!(}CF_3\phantom{CFCF_2O)_{n-1}\!-\!}X$$

wherein X is a fluorine atom or trifluoromethyl group; and n is an integer of 2–5.

2 Claims, 2 Drawing Sheets

HEXAFLUOROPROPYLENE OXIDE OLIGOTHER DERIVATIVE AND PROCESS FOR MANUFACTURE THEREOF

BACKGROUND OF THE INVENTION

The present invention relates to a novel hexafluoropropylene oxide (hereinafter referred to as "HFPO") oligoether derivative and a process for manufacture the same.

Perfluoroalkenes having a vinyl group (—CH=CH$_2$) at one end of the molecular chain, such as HFPO oligoether-group-containing ethylenes represented by the following general formula (3) are known in the art. (see, for example, U.S. Pat. No. 4,987,267)

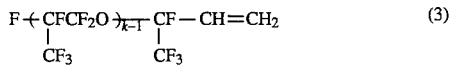

[wherein k is an integer of 2–5.]

These fluorinated compounds, which are copolymerizable to give bi- or ter-copolymers with fluoroolefins, such as tetrafluoroethylene(TFE) and perfluoroalkylvinylethers, are useful synthetic intermediates for a variety of compounds. In particular, hybrid silicone compounds obtained by hydrosilylation of these compounds are known to be extremely useful in that not only do they exhibit excellent heat resistance and low temperature characteristics, but also they are water repellent and oil repellent, and have high stain resistance and a low surface energy.

However, these fluorinated compounds, such as HFPO-oligoether-group-containing ethylenes suffer from their low reactivity and, thus have remained unsatisfactory synthetic intermediates.

SUMMARY OF THE INVENTION

It is an object of the present invention to provide a novel HFPO oligoether derivative with improved reactivities and a process for the manufacture thereof.

There is provided by the present invention HFPO oligoether derivatives represented by general formula (1) below:

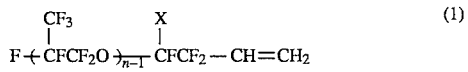

[wherein X is a fluorine atom or trifluoromethyl group; and n is an integer of 2–5.]

There is further provided by the present invention a process for the manufacture of the HFPO oligoether derivatives as set forth above comprising dehydroiodinating in the presence of a base an iodide compound represented by general formula (2) below:

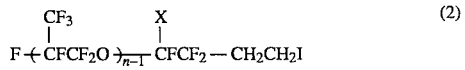

[wherein X is a fluorine atom or trifluoromethyl group; and n is an integer of 2–5.]

The HFPO oligoether derivative of the present invention, as evident from general formula (1), structurally features a primary carbon for the carbon atom adjacent to the vinyl group and, thus, is more reactive than the conventional HFPO oligoether derivatives. For example, a conventional HFPO oligoether derivative represented by general formula (3) has a secondary carbon for the carbon atom adjacent to the vinyl group. This means that the vinyl group in the HFPO oligoether derivative of the present invention suffers only little steric hindrance, which suggests improved reactivities, for example, in copolymerization with fluoroolefins, such as TFE or in hydrosilylation, thereby extremely facilitating the synthesis of a variety of fluorinated silicone compounds and the like.

DETAILED DESCRIPTION OF THE INVENTION

Figure 1:
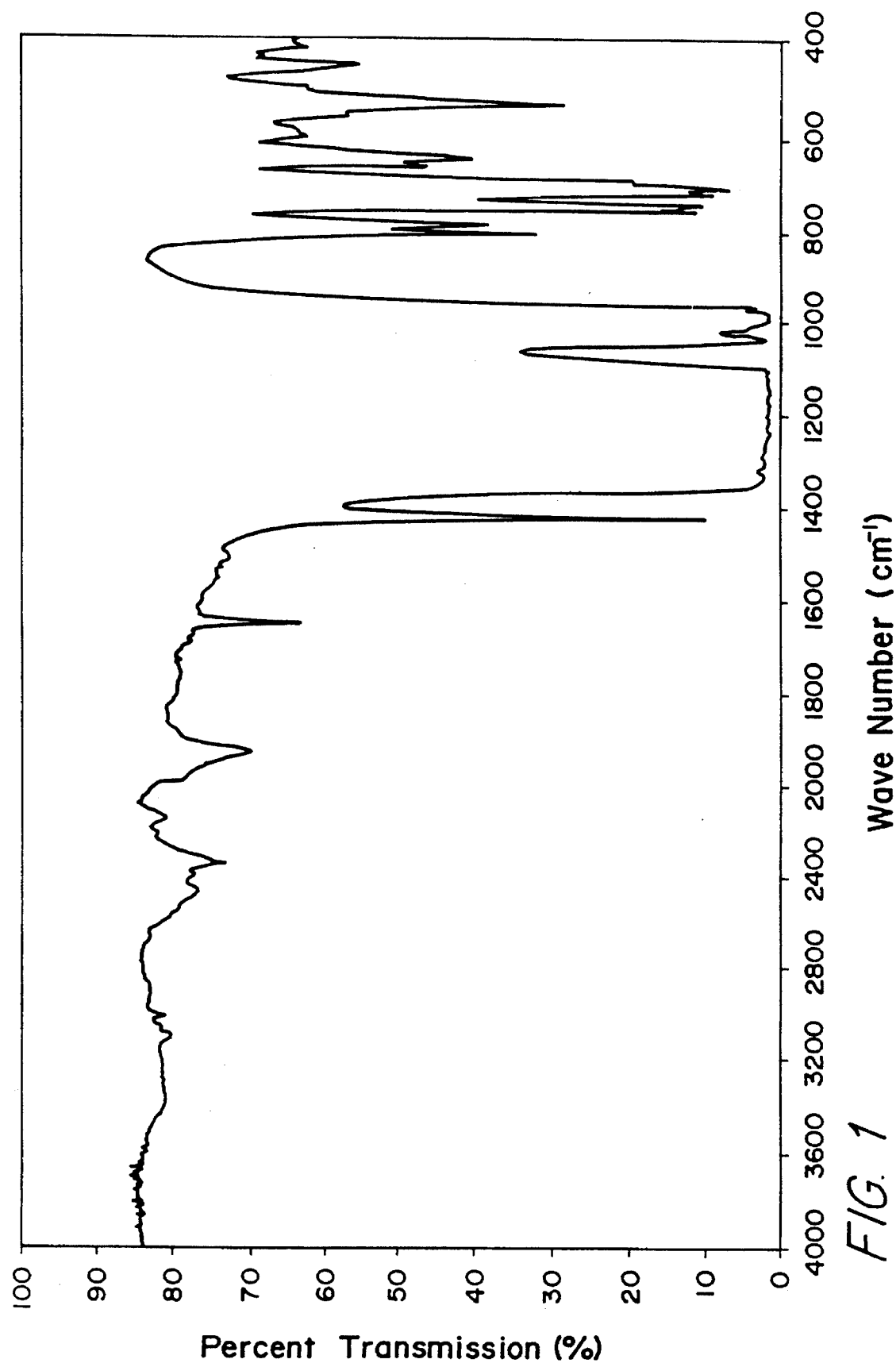
FIG. 1 is an IR spectrum of the HFPO oligoether derivative of the present invention obtained in Example 1.

The HFPO oligoether derivative of the present invention can be synthesized by dehydroiodinating in the presence of a base an iodide compound represented by general formula (2). The iodide represented by general formula (2) can be obtained, for example, by subjecting the corresponding iodide represented by general formula (4) below:

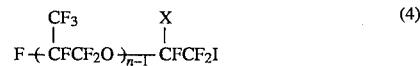

[wherein X and n are as previously defined] and ethylene to an addition reaction at 70°–80° C. in the presence of azobisisobutyronitrile (AIBN).

Examples of suitable bases to be used in the dehydroiodination reaction include alkali metal hydroxides, such as sodium hydroxide, potassium hydroxide, and cesium hydroxide, and particularly preferred examples are sodium hydroxide and potassium hydroxide.

The reactant molar ratio of the iodide of general formula (2) used in the dehydroiodination reaction and the base is ideally 1:1, but it is normally 0.5:1–10:1, preferably 0.9:1–2.5:1.

The dehydroiodination reaction is carried out by adding dropwise an iodide of general formula (2) into a solution of the above base in a suitable organic solvent. Suitable organic solvents which may be used are those capable of well dissolving the base and which are inert to the reaction and the products. Examples of suitable organic solvents are alcoholic solvents such as methanol, ethanol, n-propanol, and isopropanol, and most preferable ones are methanol and ethanol.

The dehydroiodination reaction, which is an exothermic reaction, is preferably carried out with a dropwise addition of the iodide compound of general formula (2), with the temperature of the reaction system in the range of 20°–70°C., particularly 45°–70° C. A care must be exercised so as not to make the dropwise addition rate too high, so that the reaction system temperature should not exceed the preferred temperature range. The temperature of the reaction system after completing the dropwise addition is preferably set in the range of 20°–70° C. , particularly 50°–70° C., and the reaction time after completing the dropwise addition is normally about 1–18 hours.

This reaction can be followed by gas chromatography, and the completion of this reaction can be known by the depletion of the iodide of general formula (2).

After completion of this reaction, the organic solvent and the byproduct salt are removed, followed by water washing, drying, and purifying, such as by distillation to give HFPO oligoether derivatives, represented by general formula (1).

The resultant HFPO oligoether derivatives, as explained above, are extremely reactive and highly copolymerizable to give bi- or ter-polymers with fluoroolefins, such as TFE, and the like, and fluoroalkylvinyl ethers, and the like, making them extremely useful synthetic intermediates for a variety of compounds. In particular, hybrid silicone compounds obtained by hydrosilylation of these HFPO oligoether derivatives exhibit excellent heat resistance and low temperature characteristics, water repellency and oil repellency, high staining resistance, and a low surface energy, which make them extremely useful.

EXAMPLES

The present invention is illustrated in more detail by reference to the following examples.

EXAMPLE 1

In a 10L separable flask equipped with a stirrer, a cooler, and a thermometer, was dissolved under a nitrogen stream 775 g (13.8 moles) of potassium hydroxide in 2,500 g of methanol. The solution was then heated on an oil bath to 40°–50° C., to which was added dropwise in 5.5 hours a solution of 6,000 g (10.22 moles) of an iodide of the following formula.

$$CF_3CF_2CF_2OCFCF_2OCF_2CF_2CH_2CH_2I$$
$$|$$
$$CF_3$$

After completion of the dropwise addition, the mixture was heated and stirred for about 14 hours at 70° C. The mixture was then cooled to room temperature, the salt generated was filtered off, and the bottom layer of the filtrate was separated. The separated liquid was then water washed, dried over anhydrous sodium sulfate, and distilled to give 4,171 g of the goal product (yield: 88.6%, BP: 133°–134° C./760 Torr).

The product was analyzed to give the results as shown in the following:

$^1$H-NMR: (CCl$_4$ solution, TMS internal standard, ppm)
5.7 (m, 3H, —CH=CH$_2$)
$^{19}$F-NMR: (CCl$_4$ solution, CF$_3$COOH internal standard, ppm)
—68.6 (1F, >CF—)
—53.0 (2F, CF$_3$CF$_2$CF$_2$O—)
—41.4 (2F, —CF$_2$CF$_2$CH=CH$_2$)
—11.5 (2F, —OCF$_2$CF$_2$CH=CH$_2$)
—7.1 (2F, —CF(CF$_3$)CF$_2$O)
—4.5 (8F, CF$_3$CF$_2$CF$_2$O—, —CF(CF$_3$)CF$_2$O—)
Infrared Absorption Spectrum (Liquid Film; KBr): The spectrum is given in FIG. 1.
MS(m/e):
335 (CF$_3$CF$_2$CF$_2$OCF(CF$_3$)CF$_2$—)
169 (CF$_3$CF$_2$CF$_2$—)
127 (—CF$_2$CF$_2$CH=CH$_2$)
100 (—CF(CF$_3$)—, —CF$_2$CF$_2$—)
69 (—CF$_3$)
Elemental Analysis (%):
Calculated: C: 25.86; H: 0.65; F: 69.61
Found C: 26.03; H: 0.57; F: 69.34

These results indicate the above compound to have a structural formula as follows:

$$CF_3CF_2CF_2OCFCF_2OCF_2CF_2-CH=CH_2$$
$$|$$
$$CF_3$$

EXAMPLE 2

The same reaction as that of Example 1 was carried out except for using 80.7 g (95.5 mmoles) of an iodide of the following formula:

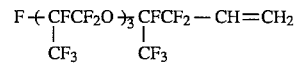

6.5 g (115.9 mmoles) of potassium hydroxide, and 21.0 g of methanol to give 57.5 g of a product (yield: 89.2%, BP: 88.5°–90.0° C./20 Torr).

Figure 2:
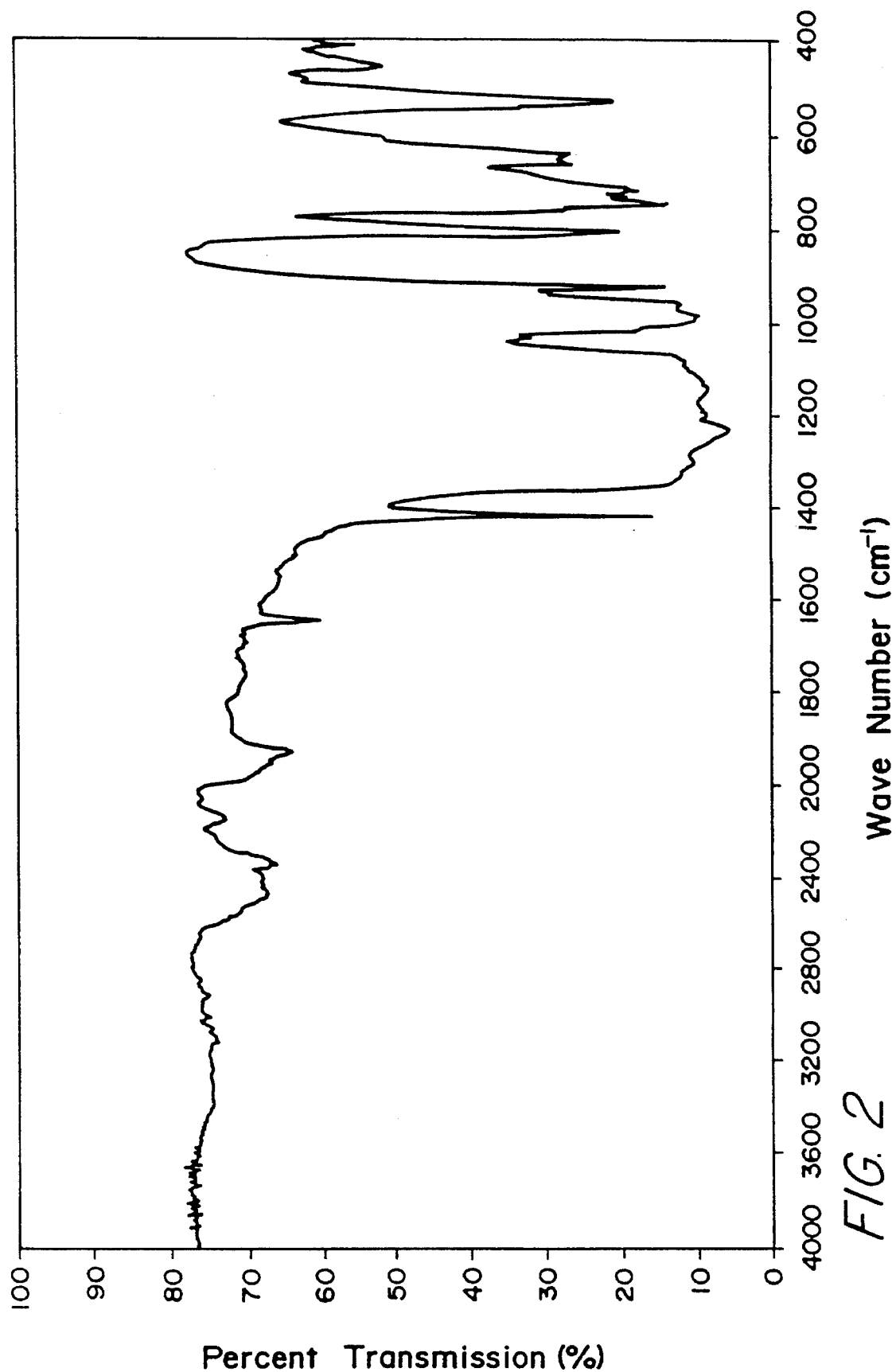
FIG. 2 is an IR spectrum of the HFPO oligoether derivative of the present invention obtained in Example 2.

The product was analyzed to give the results as shown in the following:

$^1$H-NMR: (CCl$_4$ solution, TMS internal standard, ppm)
5.8 (m, 3H, —CH=CH$_2$)
$^{19}$F-NMR: (CCl$_4$ solution, CF$_3$COOH internal standard, ppm)
—68.0 (3F, —CF(CF$_3$)CF$_2$O—)
—53.0 (2F, CF$_3$CF$_2$CF$_2$O—)
—37.2 (2F, —CF(CF$_3$)CF$_2$CH=)
—5.3 (5F, CF$_2$CF$_2$CF$_2$O—)
3.8 (10F, —[CF(CF$_3$)CF$_2$O]$_2$—)
2.7 (3F, —CF(CF$_2$)CF$_2$CH=)
Infrared Absorption Spectrum (Liquid Film; KBr): The spectrum is given in FIG. 2.
MS(m/e):
343 (—CF(CF$_3$)CF$_2$OCF(CF$_3$)CF$_2$CH=CH$_2$—)
177 (—CF(CF$_3$)CF$_2$CH=CH$_2$)
169 (CF$_3$CF$_2$CF$_2$—)
157, 113, 100 (—CF(CF$_3$)—, —CF$_2$CF$_2$—)
77 (—CF$_2$CH=CH$_2$)
69 (—CF$_3$)
Elemental Analysis(%):
Calculated: C: 24.21; H: 0.43; F: 68.44
Found C: 24.10; H: 0.52; F: 68.58

These results indicate the above compound to have a structural formula as follows:

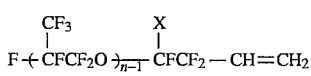

What is claimed is:

1. A hexafluoropropylene oxide oligoether derivative represented by general formula (1) below:

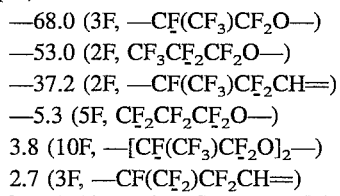

wherein X is a fluorine atom and n is an integer of 2–5.

2. The oligoether derivative of claim 1, wherein n is 3.

* * * * *

UNITED STATES PATENT AND TRADEMARK OFFICE
CERTIFICATE OF CORRECTION

PATENT NO. : 5,453,549

DATED : September 26, 1995

INVENTOR(S) : KOIKE et al.

It is certified that error appears in the above-identified patent and that said Letters Patent is hereby corrected as shown below:

title page, item [54] and column 1, line 2, "OLIGOTHER" should read
—OLIGOETHER—.

Signed and Sealed this

Twenty-eighth Day of November 1995

Attest:

BRUCE LEHMAN

Attesting Officer     Commissioner of Patents and Trademarks